(12) United States Patent
Baker et al.

(10) Patent No.: US 7,481,822 B1
(45) Date of Patent: Jan. 27, 2009

(54) ENDOVASCULAR GRAFT FOR PROVIDING A SEAL WITH VASCULATURE

(75) Inventors: Steven G. Baker, Sunnyvale, CA (US); Tamara L. Trayer, Belmont, CA (US); Arnold M. Escano, Santa Clara, CA (US); Mark LeMere, Mountain View, CA (US); Elizabeth A. McDermott, San Carlos, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 256 days.

(21) Appl. No.: 10/796,543

(22) Filed: Mar. 8, 2004

Related U.S. Application Data (62) Division of application No. 09/559,681, filed on Apr. 27, 2000, now Pat. No. 6,729,356.

(51) Int. Cl.
*A61M 29/00* (2006.01)
(52) U.S. Cl. .................................... 606/198
(58) Field of Classification Search ................ 623/1.1, 623/1.12, 1.13, 1.22, 1.23, 1.24, 1.35, 1.36; 606/19–198
See application file for complete search history.

(56) References Cited

U.S. PATENT DOCUMENTS

| | | | |
|---|---|---|---|
| 3,908,662 A | 9/1975 | Razgulov et al. | |
| 4,148,664 A | 4/1979 | Cruz | |
| 4,214,587 A | 7/1980 | Sakura, Jr. | |
| 4,394,373 A | 7/1983 | Malette et al. | |
| 4,631,188 A | 12/1986 | Stoy et al. | |
| 4,640,279 A | 2/1987 | Beard | |
| 4,641,653 A | 2/1987 | Rockey | |
| 4,652,263 A | 3/1987 | Herweck et al. | |
| 4,693,249 A | 9/1987 | Schenck et al. | |
| 4,740,207 A | 4/1988 | Kreamer | |
| 5,122,135 A | 6/1992 | Durr et al. | |
| 5,156,620 A | 10/1992 | Pigott | |
| 5,192,310 A | 3/1993 | Herweck et al. | |
| 5,221,259 A | 6/1993 | Weldon et al. | |
| 5,262,974 A | 11/1993 | Hausmann et al. | |
| 5,282,847 A | 2/1994 | Trescony et al. | |
| 5,330,528 A | 7/1994 | Lazim | |
| 5,383,926 A | 1/1995 | Lock et al. | |
| 5,415,657 A | 5/1995 | Taymor-Luria | |
| 5,443,499 A | 8/1995 | Schmitt | |

(Continued)

FOREIGN PATENT DOCUMENTS

WO     WO 97/13717     2/1997

*Primary Examiner*—Kevin T Truong
(74) *Attorney, Agent, or Firm*—RatnerPrestia (57) ABSTRACT

A graft provided with a flexible sealing member to substantially prevent blood from leaking between the graft a lumen into which the graft is placed. In one embodiment, the flexible sealing member may be pressed against the vascular wall by an outwardly biased spring means attached to the sealing member. In other embodiments, the sealing member may be self-positioning upon deployment of the graft. The sealing member also may be formed into the shape of a toroid, which may be filled with thrombogenic material causing blood permeating into the toroid-shaped space to coagulate therein and hold the sealing member in place. It is also contemplated that the sealing member be formed from tufts of frayed yarn protruding circumferentially from the outer surface of the graft. A method of manufacturing such tufted yarn sealing members is also disclosed.

8 Claims, 11 Drawing Sheets

U.S. PATENT DOCUMENTS

| | | |
|---|---|---|
| 5,476,506 A | 12/1995 | Lunn |
| 5,522,881 A | 6/1996 | Lentz |
| 5,534,024 A | 7/1996 | Rogers et al. |
| 5,540,715 A | 7/1996 | Katsaros et al. |
| 5,554,180 A | 9/1996 | Turk |
| 5,556,413 A | 9/1996 | Lam |
| 5,562,727 A | 10/1996 | Turk et al. |
| 5,582,619 A | 12/1996 | Ken |
| 5,607,464 A | 3/1997 | Trescony et al. |
| 5,618,299 A | 4/1997 | Khosravi et al. |
| 5,624,669 A | 4/1997 | Leung et al. |
| 5,649,949 A | 7/1997 | Wallace et al. |
| 5,653,370 A | 8/1997 | Bereiter et al. |
| 5,665,117 A * | 9/1997 | Rhodes ................ 623/1.1 |
| 5,667,767 A | 9/1997 | Greff et al. |
| 5,676,689 A | 10/1997 | Kensey et al. |
| 5,676,696 A * | 10/1997 | Marcade ............... 623/1.35 |
| 5,693,088 A | 12/1997 | Lazarus |
| 5,769,882 A | 6/1998 | Fogarty et al. |
| 5,785,679 A | 7/1998 | Abolfathi et al. |
| 5,827,310 A | 10/1998 | Marin et al. |
| 5,860,948 A | 1/1999 | Buscemi |
| 5,871,537 A | 2/1999 | Holman et al. |
| 5,873,906 A | 2/1999 | Lau et al. |
| 5,876,419 A | 3/1999 | Carpenter et al. |
| 5,893,859 A | 4/1999 | Marin et al. |
| 5,919,225 A | 7/1999 | Lau et al. |
| 5,925,683 A | 7/1999 | Park |
| 5,935,148 A | 8/1999 | Villar et al. |
| 5,941,888 A | 8/1999 | Wallace et al. |
| 5,944,750 A | 8/1999 | Tanner et al. |
| 5,951,599 A | 9/1999 | McCrory |
| 5,993,489 A | 11/1999 | Lewis et al. |
| 5,997,556 A * | 12/1999 | Tanner .................. 606/153 |
| 6,007,575 A | 12/1999 | Samuels |
| 6,015,429 A | 1/2000 | Lau et al. |
| 7,166,120 B2 * | 1/2007 | Kusleika ................ 606/191 |

* cited by examiner

ENDOVASCULAR GRAFT FOR PROVIDING A SEAL WITH VASCULATURE

This application is a divisional of application Ser. No. 09/559,681, filed Apr. 27, 2000 now U.S. Pat. No. 6,729,356.

BACKGROUND OF THE INVENTION

The present invention relates generally to medical devices, and more particularly to methods and apparatus for the endoluminal placement of tubular prostheses, such as grafts, for repairing aneurysms or other vascular defects in humans and animals.

Aneurysms are discrete dilations of the arterial wall, caused by weakening of the arterial wall. One of the most common, and among the most life threatening, is an aneurysm of the abdominal aorta between the renal and iliac arteries. If untreated, the aneurysm dilates progressively with an ever increasing risk of rupture and hemorrhagic death.

One method of treatment is provided by direct surgical intervention, in which the defective vessel may be bypassed or replaced using a prosthetic device such as a synthetic graft. The risks involved in direct surgical intervention of this magnitude are great, and include an extensive recovery period.

In recent years a less invasive method of treatment has evolved through a series of inventions. The details vary, but, conventionally, a resilient tubular conduit fashioned from flexible fabric (herein referred to as a "graft") is introduced into the defective vessel by means of catheters introduced into the femoral artery. The graft is attached to the non-dilated or slightly dilated arteries above and below the aneurysm using expandable metallic cylinders (herein referred to as "attachment systems") which may include barbs or hooks to enhance attachment to the vascular wall.

When an attachment system is positioned on the interior of a graft's lumen, it will tend to cause the outer wall of the graft to press against the inner wall of the vessel, thereby providing the additional function of providing a seal, preventing fluid flow to the region between the graft and the vascular wall.

However, the use of generally cylindrical grafts to reinforce vascular walls in a patient is not without problems. Grafts are required to be compressed into a catheter before being delivered and deployed into final position. Furthermore, grafts compressed into a catheter for delivery must be capable of bending around corners and branches of the patient's vascular system. The graft must accordingly be sufficiently flexible to satisfy these requirements.

One of the challenges encountered with the use of a flexible graft is that, because a diseased vessel is often irregularly shaped, the ends of the graft, even when urged outwardly by an attachment system, may not have a continuous circumferential edge pressed firmly against the inner wall of the vessel. As a result, fluid may leak into or out of (through a branch vessel) the region between the graft and the vascular wall, thereby increasing fluid pressure on the weakened walls of the vessel and reducing the protective effect of the graft. The same problem will occur if, as a result of an error in pre-operative sizing of the diseased vessel, a graft is provided that has a diameter slightly smaller than the diameter of the diseased vessel. Moreover, in the event the target vessel changes shape over time (ie., increase in neck diameter or shrinkage in aneurysm), perigraft flow may occur. It will be appreciated that in these situations, because the fabric from which grafts are conventionally made is not circumferentially expandable, a complete seal around the circumference of the vessel will likely not be achieved.

Accordingly, there is a need for an improved graft that provides an enhanced seal for substantially preventing the flow of blood into the region between the graft and the vascular wall.

SUMMARY OF THE INVENTION

Briefly, and in general terms, an intraluminal graft in accordance with the present invention is structured to provide an enhanced seal between the graft and the wall of a lumen within which the graft is implanted. The graft of the present invention generally comprises a tubular member, at least one expandable attachment system connected to the tubular member, and at least one expandable sealing member connected to an exterior wall of the tubular member.

In one aspect of the invention, the graft of the present invention is adapted to be radially compressed to a reduced diameter to facilitate insertion into a patient's vasculature and for advancement within the vasculature to a desired location. The graft is further adapted to be radially expandable from its compressed condition to an expanded condition for engagement with the vascular wall, and thus, the graft is contemplated to be made from a biocompatible material. In further embodiments, the graft may be bifurcated to have left and right branches, each with an opening at an inferior end.

The attachment system of the present invention is configured to have a generally cylindrical profile, and is adapted to be radially compressed to a reduced diameter. The attachment system is radially expandable from its compressed condition to an expanded condition, to facilitate implantation of a graft within vasculature. At least one attachment system is connected to the wall of the graft, at a superior end portion thereof. In further embodiments, additional attachment systems may be connected to the graft to provide additional attachment to the vascular wall as desired.

According to one embodiment of the present invention, a sealing member manufactured from a generally flexible fabric and having a frusto-conical shape is connected to an exterior wall of the tubular member of the graft. The sealing member is supported by a biasing member which may be formed from a generally undulating wire frame configured to provide the frusto-conical profile of the sealing member and to impart an outward bias sufficient to compress the sealing member against the vasculature. The sealing member advantageously provides the graft with the ability to expand to assume the shape of the vasculature at the target site, thereby preventing fluid flow into the region between the graft and the vascular wall.

In a second embodiment of the invention, the graft is configured with a sealing member that is adapted to cooperate with the outward expansion of an attachment system of the graft so that, upon deployment of the graft, the sealing member is moved from a first position remote from the attachment system to a second position overlapping the attachment system. In the deployed state, the sealing member of this embodiment cooperates with fluid flow to enhance the seal between tubular member and vascular wall. Additionally, tufted yarn possibly impregnated with thrombogenic material may be attached to the sealing member, thereby further enhancing the sealing effect.

In a third embodiment, the improved graft is adapted with a sealing member that has a flexible disk configuration. In this embodiment, a generally undulating biasing member provides the sealing member with an outward bias. The outward bias of the wire frame causes the sealing member to be pressed against the wall of the vessel, substantially preventing leakage between sealing member and vascular wall.

In a fourth embodiment, there is provided a disk-shaped sealing member, an outer circular edge of which is configured with a wire hoop biasing member. The wire hoop biasing member is packed into a delivery capsule by folding the hoop into a generally zig-zag shape. When deployed from the delivery capsule, the wire hoop unfolds into a circular profile to thereby substantially prevent leakage between sealing member and vascular wall.

In a fifth embodiment, the sealing member has a toroid shape, the outer surface of which is made from a flexible fabric, and the interior of which may be filled with a thrombogenic material such as polyester filaments. It is to be recognized that the seal fabric may be very thin compared to graft since the seal fabric only needs to initiate clotting. The toroid-shaped sealing member is configured to fill with the patient's blood which will subsequently coagulate with the thrombogenic material, thereby creating a rigid obstacle to the flow of blood between sealing member and the vascular wall. In another aspect of the invention, thrombogenic filling material may be introduced into the toroid-shaped interior of the sealing member after the graft has been delivered to a desired position in the patient's vasculature. Additionally, small apertures may be created in a wall between the graft and sealing member so that the sealing member fills with blood flowing from the interior of the graft.

In a sixth embodiment, the sealing member may be formed entirely from tufts of yarn which are fixed to the outer surface of the graft. A method of manufacturing such a graft is also disclosed.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

In general, the present invention involves configuring a graft with a sealing member that operates to occupy spaces between the graft and a lumen into which the graft is implanted. The preferred embodiments of the improved graft are described below. Although the descriptions set forth below generally relate to configuring a proximal end of a graft with a sealing member, the improvement may be applied to the distal end of a graft as well. Where the graft is bifurcated, the disclosed sealing members may be applied to any or all of the ends of such a graft. The term "proximal" as used herein shall mean upstream, while "distal" shall mean downstream.

Figures 1, 2:
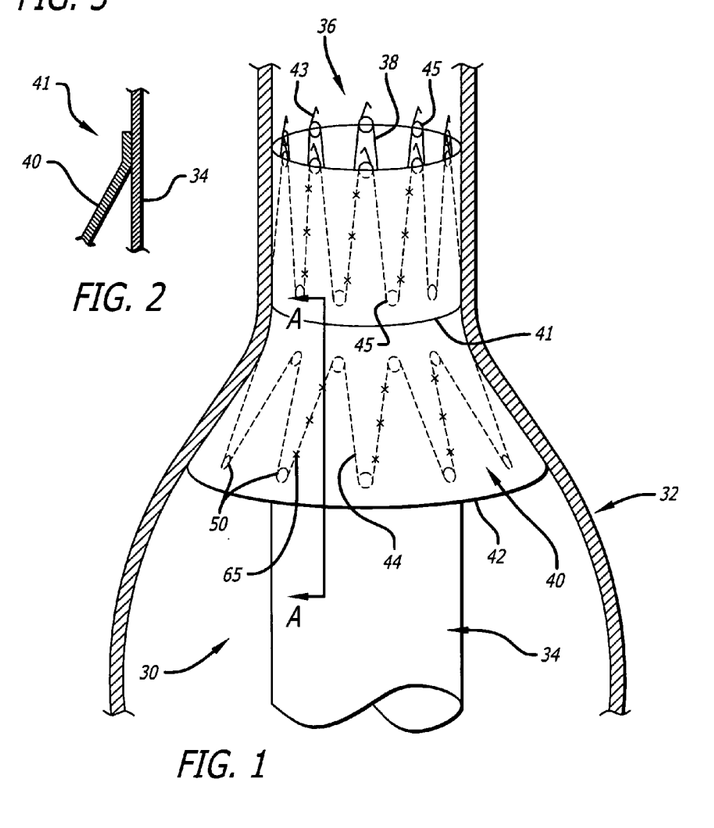
FIG. 1 is a cross-sectional view, depicting one embodiment of a graft of the present invention, configured with a frusto-conical sealing member.
FIG. 2 is a cross-sectional view, taken along line A-A of FIG. 1.

FIG. 1 exemplifies a proximal end portion of one embodiment of a graft 30 of the present invention positioned within a vessel 32 of a patient. The vessel 32 is shown to expand from a relatively narrow diameter healthy section to a dilated section where the tissue is diseased. The improved graft 30 comprises a tubular member 34 having a proximal end 36 and distal end (not shown in FIG. 1), at least one expandable attachment system 38, and a generally frustrum-shaped sealing member 40 supported by a biasing member 44. The attachment system 38 is connected to the tubular member 34 adjacent the proximal end 36 of the graft 30.

As shown in FIGS. 1 and 2, the sealing member 40 includes an inner circumferential edge 41 and an outer circumferential edge 42, the inner circumferential edge 41 being connected to an outside surface of the tubular member 34. In one embodiment, the point of connection between the sealing member 40 and tubular member 34 is longitudinally separated from the attachment system 38, so as to minimize the outer profile of the graft assembly 30 when it is compressed for insertion into vasculature.

The tubular member 34 and the sealing member 40 are contemplated to be manufactured from any flexible surgical implantable material such as Dacron™ which is known to be sufficiently biologically inert, non-soft biodegradable, and durable. One material found to be satisfactory is DeBakey soft woven Dacron™ vascular prosthesis (uncrimped) sold by USCI. In order to prevent the woven material from unraveling at the ends, the ends can be melted with heat to provide a small melted bead of Dacron™.

The attachment system 38 may be either self expanding or balloon-expanded, and may be connected, preferably, but not necessarily, to an inner wall of the tubular member 34. As shown in FIG. 1, the attachment system 38 may have a plurality of hooks 43 connected to it to enhance attachment to the vascular wall. The attachment system 38 is made from a wire formed into an undulating configuration defining opposing apices. In a preferred embodiment, the apices include helical springs 45.

Figure 3:
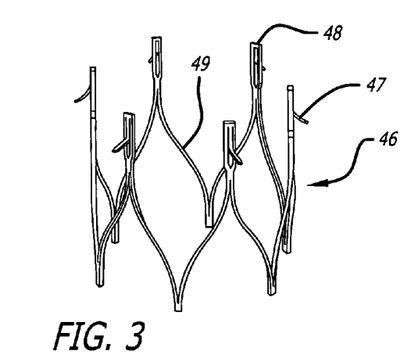
FIG. 3 is a perspective view, depicting an alternative embodiment of an attachment system.

With reference to FIG. 3, there is shown an alternative embodiment of an attachment system 46. In this embodiment, the attachment system 46 includes hooks 47 which are integrally formed at proximal apices 48. The attachment system 46 is further characterized by having a semi or generally flat wire configuration, in that members 49 have a depth that is greater than its width. In a preferred method of manufacture, the flat wire attachment system 46 is contemplated to be laser cut from a tube.

Figure 4:
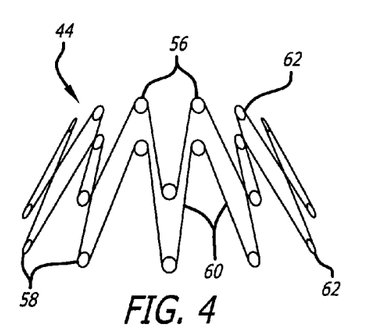
FIG. 4 is a perspective view depicting a biasing member.

With reference to FIG. 4, the biasing member 44 may be formed from a wire which follows a generally undulating path, producing a plurality of alternating inner apices 56 and outer apices 58 which are joined by connecting members or legs 60. The biasing member 44 has a generally frusto-conical profile and is shown connected to the inside surface of the sealing member 40; however, it can alternatively be attached to an outside surface. The biasing member 44 serves to urge the sealing member 46 from a first compressed position to a second expanded position. When the biasing member 44 is compressed stored energy tends to urge legs 60 and apices 56, 58 radially outward in a direction generally at a right angle to a longitudinal axis of the device. The biasing member 44 provides a continuous and outwardly directed urging force, pressing the sealing member 40 against the diseased vascular wall 32, to thereby obstruct the flow of blood into the region between the tubular member 34 and the vascular wall 32.

The generally undulating shape of the wire frame forming the biasing member 44 also serves to facilitate compression of the biasing member 44 when it is placed within a delivery capsule (not shown). The compression of the biasing member 44 may be accomplished by compressing the biasing member 44 within its elastic limit. Placing selected inner and outer apices 45 in different planes aids in reducing the size to which the biasing member 44 can be compressed. Additionally, incorporating helical springs 62 at the apices 56, 58 aids in the self-expansion of the biasing member 44. For tubular members 34 configured with larger diameter sealing members 40, the biasing member 44 can be provided with additional apices 56, 58 to enhance the sealing effect.

The biasing member 44 may be formed of a corrosion resistant material that has good spring and fatigue characteristics. One such material found to be particularly satisfactory is Elgiloy™ which is a chromium-cobalt-nickel alloy manufactured and sold by Elgiloy of Elgin, Ill. Another suitable material is Nitinol.

It will be appreciated that the biasing member 44 has the ability to automatically adjust to various shapes of diseased vessel walls 32 or changes in anatomy shape or position over time. This ability is an important design feature, because it may not be possible to accurately predict the shape of the diseased vessel 32 into which the improved graft 30 is delivered, and also because the wall of the diseased vessel 32 may undergo changes in shape due to cardiac pulsation or other movements of the patient. By adjusting to the actual profile of the diseased vessel wall 32, the biasing member 44 and the sealing member 40 substantially prevent leakage of blood into the region between tubular member 34 and vessel wall 32.

The biasing member 44 may be secured to the sealing member 40 by suitable connecting means 65, such as Dacron™ polyester sutures, by which the biasing member 44 may be sewn or stitched onto the sealing member 40. Connection can be accomplished by sewing suture material into and out of the wall of the sealing member and by forming knots on one or more of the biasing member's legs 50. The attachment system 38 may be similarly connected to the tubular member 34 using polyester suture connecting means 65.

Turning now to FIGS. 5-8, another embodiment of an improved graft 130 of the present invention is described. The graft 130 embodies a tubular member 134, an attachment system 138, and a sealing member 140. The attachment system 138 may embody the undulating wire or flat wire configuration described above, or any other suitable expandable frame arrangement. The attachment system 138 is connected to the tubular member 134, adjacent a proximal end thereof.

The sealing member 140 has a generally frusto-conical shape with an inner circumferential edge 141 and an outer circumferential edge 142. The inner circumferential edge 141 is connected at an outside surface of the tubular member 134. Additionally, pieces of tufted yarn 157, preferably impregnated with a thrombogenic substance, may be attached to the sealing member 140. The point of connection between tubular member 134 and sealing member 140 is preferably positioned medical to the attachment system 138 to keep the compressed diameter of the assembly small.

Figure 5:
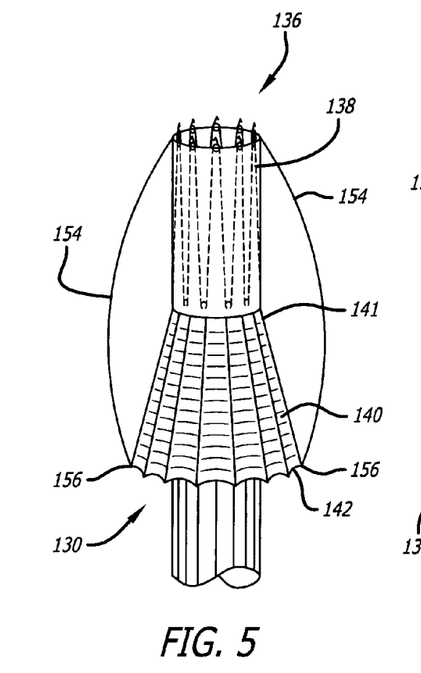
FIG. 5 is a perspective view, depicting a second embodiment of a graft configured with a frustrum-shaped sealing member.
Figure 6:
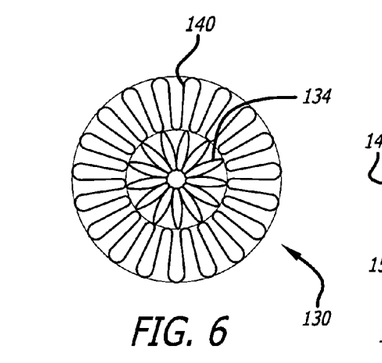
FIG. 6 is a top view of the graft shown in FIG. 5.

As shown in FIGS. 5 and 6, to facilitate packing the improved graft 130 into a delivery tube device (not shown), the tubular member 134 and sealing member 140 are positioned in first compressed conditions, wherein the outer circumferential edge 142 of the sealing member 140 is folded away from the proximal end 136 of the tubular member 134. Folding the sealing member 140 in this manner has the advantage of reducing the overall outside profile of the graft assembly 130 when it is placed in a compressed condition. At least one thread 154 with first end 156 and second end 158 (See FIG. 8) is provided and are attached to the outer circumferential edge 142 of the sealing member 140. The second ends 158 of the threads 154 are first passed sequentially through a number of the outer eyelets 151 formed at the proximal apices of the attachment system 138, and are then connected to the graft 130. It is contemplated that a monofilament polypropylene thread 154 can be employed, and that the optimal number of threads to use in order to avoid entanglement is three.

Figure 7:
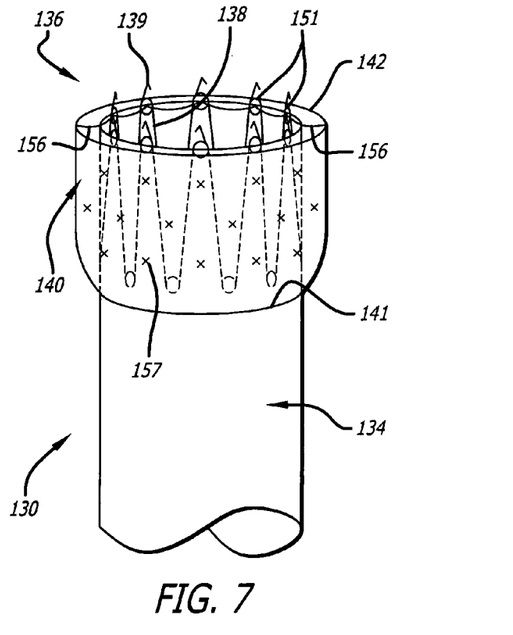
FIG. 7 is a perspective view of the graft shown in FIG. 5 in a deployed state.
Figure 8:
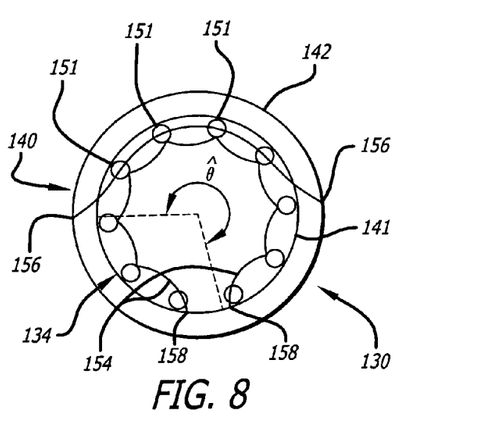
FIG. 8 is a top view of the graft shown in FIG. 7.

It will be appreciated that when the graft 130 is deployed from its compressed condition and the attachment system 138 is activated to expand outward, the first ends 156 of the threads 154, together with the outer edge 142 of the sealing member, are pulled toward the proximal end 136 of the tubular member. Thus, the sealing member 140 in its deployed state, overlaps the attachment system 138 to thereby benefit from the outward bias of the attachment system 138 and to sealingly engage the vasculature. It will be appreciated that the tufted yarn 157 attached to the sealing member 140 can enhance the seal with the vascular tissue when compressed against the tissue by the attachment system 138. Additionally, it is also to be recognized that the tubular yarn 157 may also bunch up at the attachment system 138 and still work as intended.

The number of outer eyelets 151 through which the second ends 158 of the threads 154 are passed will depend on the displacement required to move the outer circumferential edge 142 of the sealing member from its first undeployed position to its final deployed position. The amount of proximal axial displacement that the first end 156 of each thread will experience upon expansion of the attachment system may be expressed as $(D_{expanded} - D_{compressed}) * \theta_{wrap}/2$, where $D_{expanded}$ is the diameter of the attachment system 138 in expanded condition, $D_{compressed}$ is the diameter of the attachment system 138 in compressed condition, and $\theta_{wrap}$ (See FIG. 8) is the angle (in radians) extended to the center of the attachment system by that portion of thread 154 which winds around the circumference of the attachment system passing through the eyelets 151.

Figure 9:
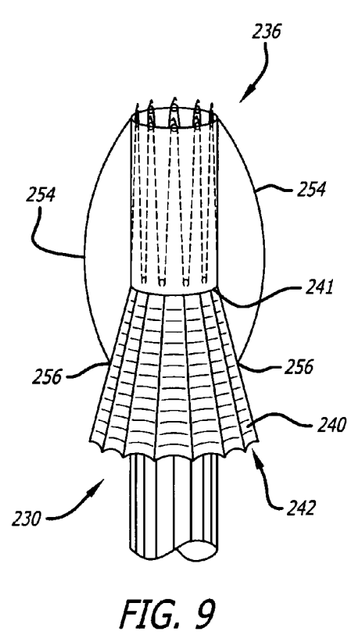
FIG. 9 is a perspective view, depicting a variation of the embodiment of the graft of FIG. 5.
Figure 10:
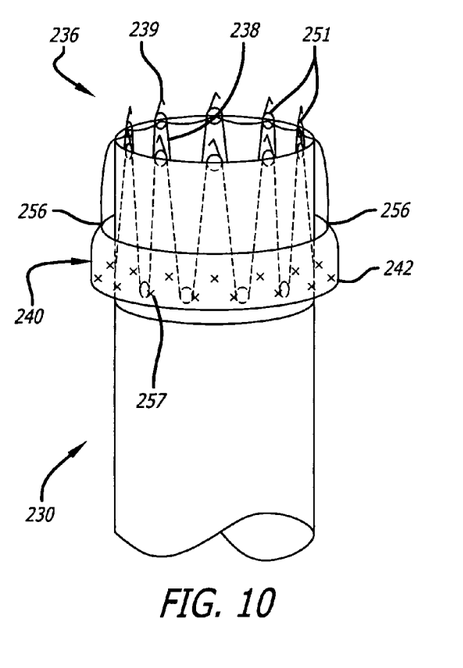
FIG. 10 is a perspective view of the graft shown in FIG. 9 shown in a deployed state.

A variation of the graft 130 shown in FIGS. 5-8 is depicted in FIGS. 9 and 10. In this embodiment, a first end 256 of each thread 254 is connected to a point on the sealing member 240 between an inner edge 241 and an outer edge 242. It will be appreciated that as so configured, the sealing member 240 will be pulled proximally as the attachment system 238 expands, but that the outer edge 242 will extend distally of the point of connection between thread 254 and sealing member 240. Thus, in a deployed condition, there are two layers of fabric between a vascular wall and the tubular member 230. Consequently, a thicker layer of tufted material 257 may be sandwiched between the vascular wall and the tubular member 230 to facilitate forming a seal.

Figure 11:
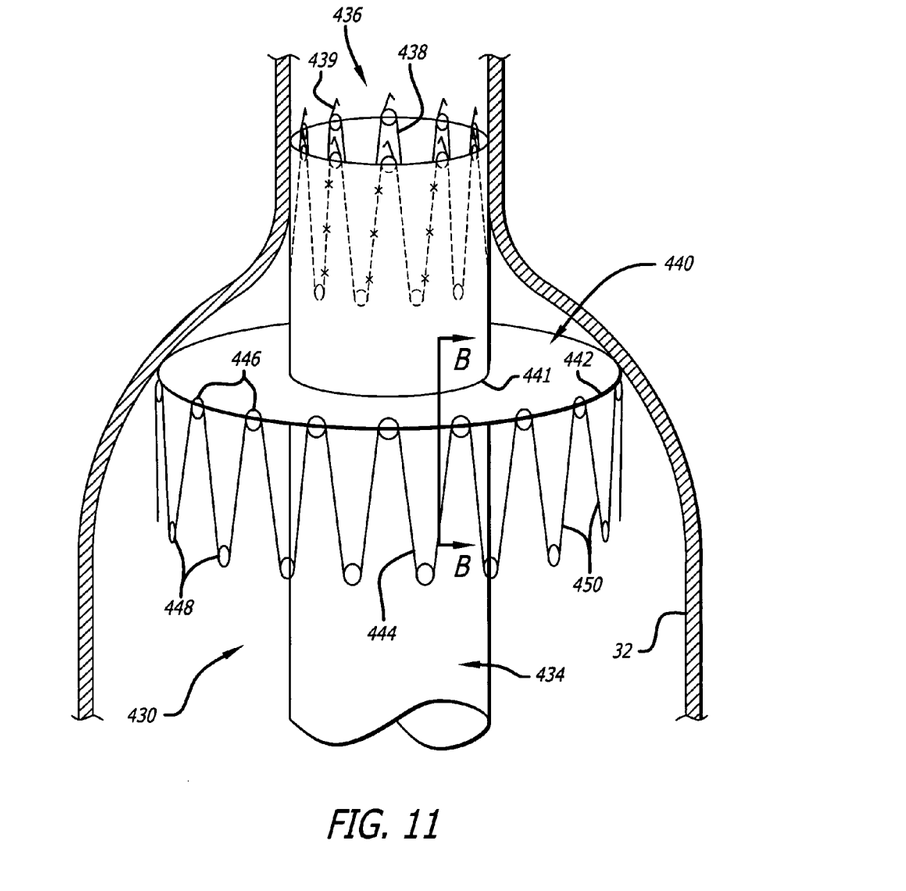
FIG. 11 is a cross-sectional view, depicting a third embodiment of the graft of the present invention configured with a disk-shaped sealing member.

With reference to FIG. 11, another embodiment of an improved graft 430 of the present invention is shown. In this embodiment, the tubular member 434 and attachment system 438 have a similar configuration as the same of the previously described embodiments. The tubular member 434 is connected to a sealing member 440 supported by a wire frame biasing member 444. The sealing member 440 may be made from the same flexible material as the sealing members of the previous embodiments, allowing the sealing member to assume both a compressed condition and an expanded condition. The sealing member 440 of this embodiment, however, has a disk shape with an inner circumferential edge 441 and an outer circumferential edge 442.

Figure 12:
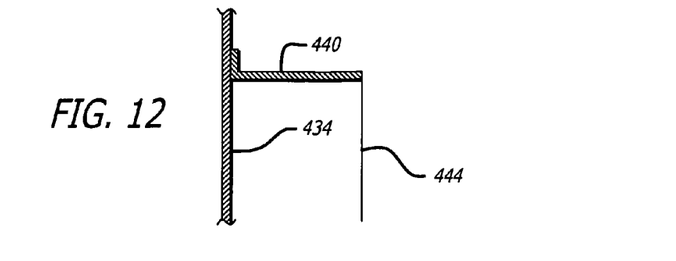
FIG. 12 is a sectional view taken along lines B-B of FIG. 11.

As exemplified in FIG. 12, the inner circumferential edge 441 of the sealing member 440 is continuously connected to an outer surface of the tubular member 434. The point of connection between tubular member 434 and sealing member 440 is preferably positioned so as not to coincide with the attachment system 438. The wire frame biasing member 444 may be made of the same wire material as the biasing members of the previous embodiments and accordingly, may have a frusto-conical shape. Alternatively, as shown in FIG. 11, it is contemplated that the biasing member 440 can define a generally cylindrical expanded profile, with alternating inner apices 446 and outer apices 448 joined by struts 450. When the wire frame 444 is compressed, stored energy tends to urge the struts 450 and apices 446, 448 of the wire frame 444 radially outward.

The inner apices 446 of the wire frame biasing member 444 is attached to the outer circumferential edge 442 of the sealing member 440, the outer apices 448 being allowed to protrude in an inferior direction. The biasing member 444 is adapted to provide an outward bias to the sealing member 440, thereby causing the outer edge 442 of the sealing member 440 to press against the diseased vascular wall 32, and substantially prevent leakage of blood between the tubular member 434 and the vascular wall 32.

Figures 13, 14:
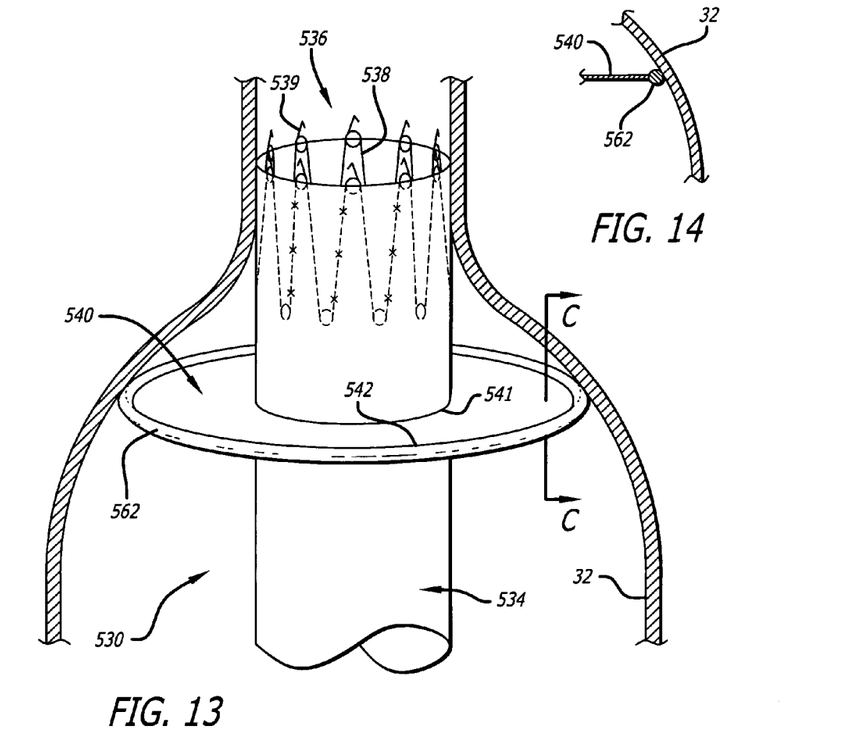
FIG. 13 is a perspective view, depicting a fourth further embodiment of the graft of the present invention, configured with a disk-shaped sealing member.
FIG. 14 is a sectional view taken along lines C-C of FIG. 13.
Figure 15:
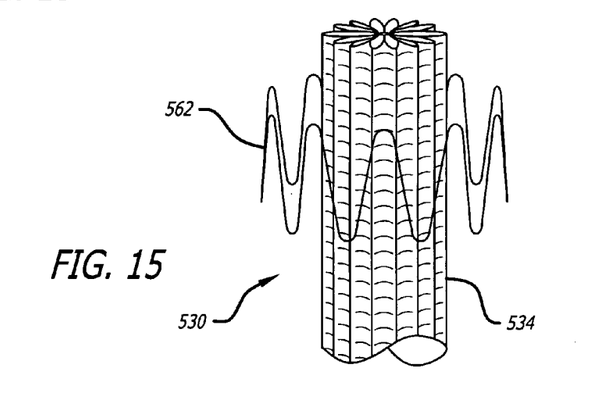
FIG. 15 is a perspective view of the graft shown in FIG. 11, in a compressed condition.

As shown in FIGS. 13-15, another embodiment of a graft 530 of the present invention includes a disk-shaped sealing member 540. In this aspect of the invention, the sealing member 540 may be supported by a wire hoop 562 with a generally radially outward spring bias. The outer circumferential edges 542 of the sealing member 540 is contemplated to be connected to the wire hoop 562. Connection may be achieved by any suitable means such as by stitching the two elements together with polyester filaments.

As shown in FIG. 15, the wire hoop 562 may be compressed for loading into a delivery capsule (not shown), by configuring the hoop 562 into a generally zig-zag shape. The wire hoop 562 may be made of a corrosion resistant material with good spring properties, such as Nitinol™. The wire hoop 562 is fabricated to have a diameter slightly larger than that of the blood vessel 32, so as to provide a continuous contact therewith and to substantially prevent leakage of blood between tubular member 534 and a vessel wall 32.

Figure 16:
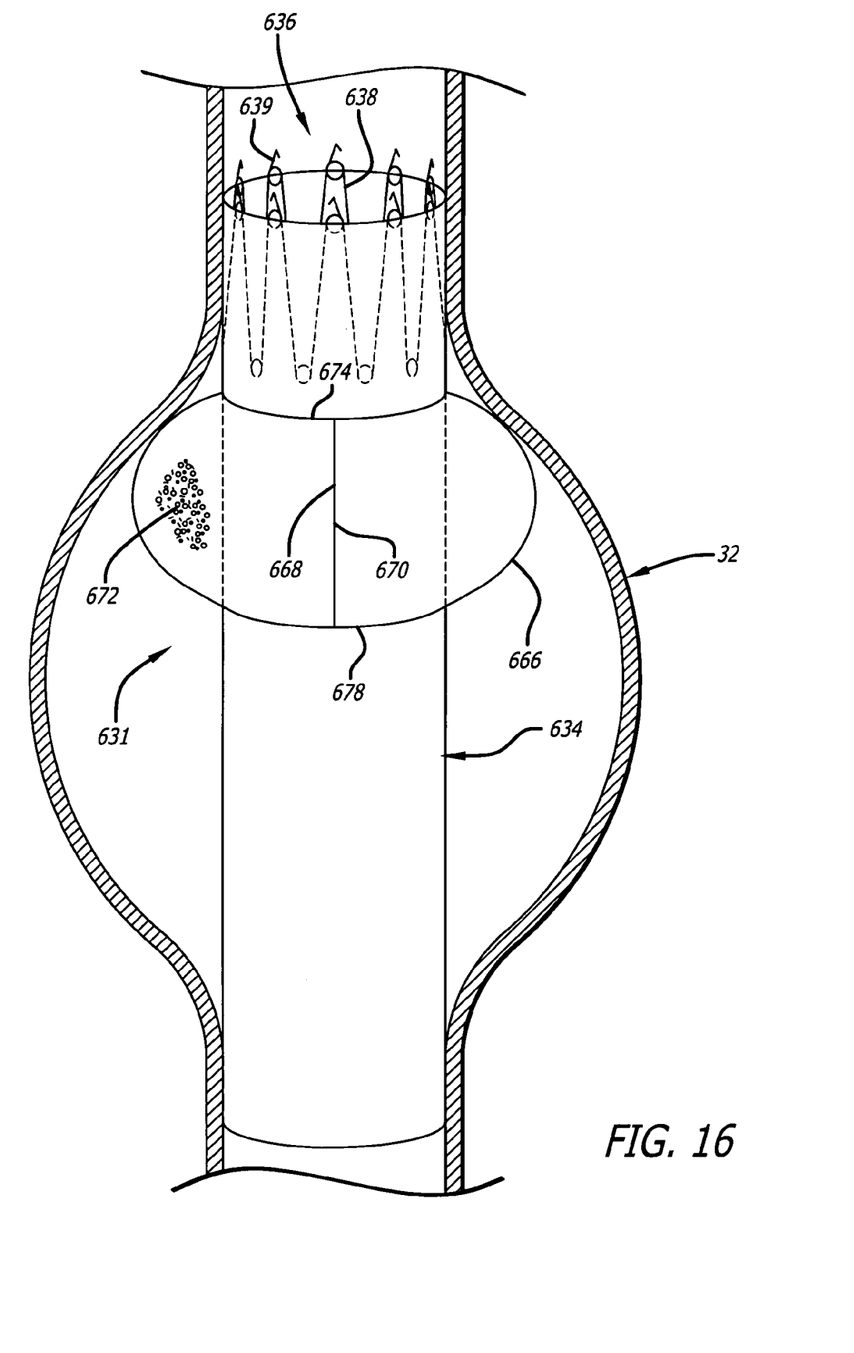
FIG. 16 is a cross-sectional view, depicting a fifth embodiment of the graft of the present invention configured with a toroid-shaped sealing member.

Yet a further embodiment of an improved graft 631 is shown in FIG. 16. The graft 631 of this embodiment includes a tubular member 634 as well as an attachment system 638 similar to that of the previous embodiments. In this embodiment, a toroid-shaped sealing member 666 which may be made from thrombogenic material, is fixed to an outer wall of the tubular member 634. The sealing member 666 may be sufficiently porous to permit blood to percolate through it. A compressible thrombogenic material 672 may be introduced into an interior of the toroid-shaped sealing member 666. When deployed in the patient, it is contemplated that blood will slowly permeate through the porous fabric of the sealing member 666 and coagulate with the thrombogenic material 672 to thereby stiffen the sealing member 666. This results in forming a seal between the tubular member 634 and the vascular wall 32.

Further, it is contemplated that the sealing member 666 may be made from planar fabric which is initially generally rectangular, with superior ends 674 and inferior ends 678 and two lateral edges 668, 670. The superior 674 and inferior ends 678 are continuously circumferentially connected to the outer wall of the tubular member 634. The lateral edges 668, 670 are connected to each other, thereby forming an enclosed toroid-shaped space in which the wall of the tubular member 634 partly encloses the toroid-shaped space. This form has the advantage of minimizing the number of fabric layers the graft 631 will have in its compressed condition.

Figure 17:
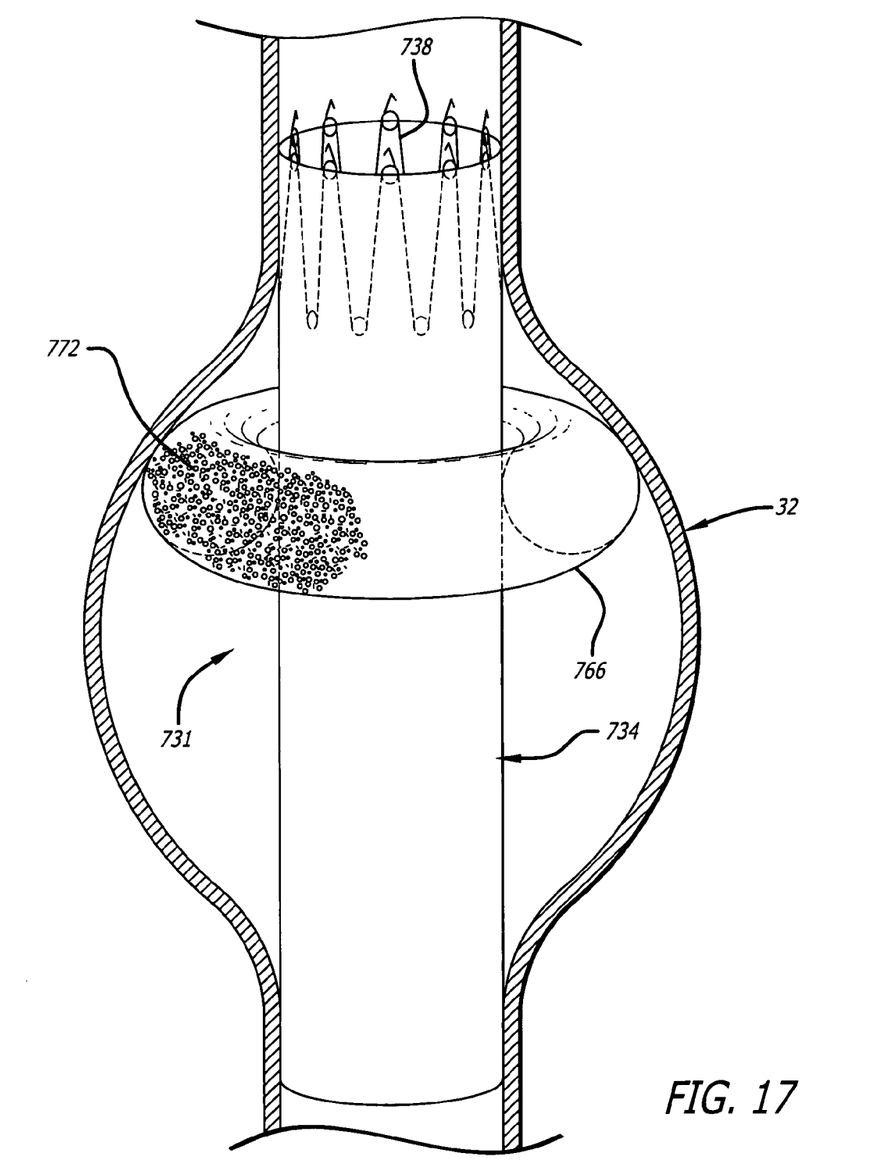
FIG. 17 is a cross-sectional view, depicting the graft of the present invention configured with a variation of a toroid-shaped sealing member.
Figure 18:
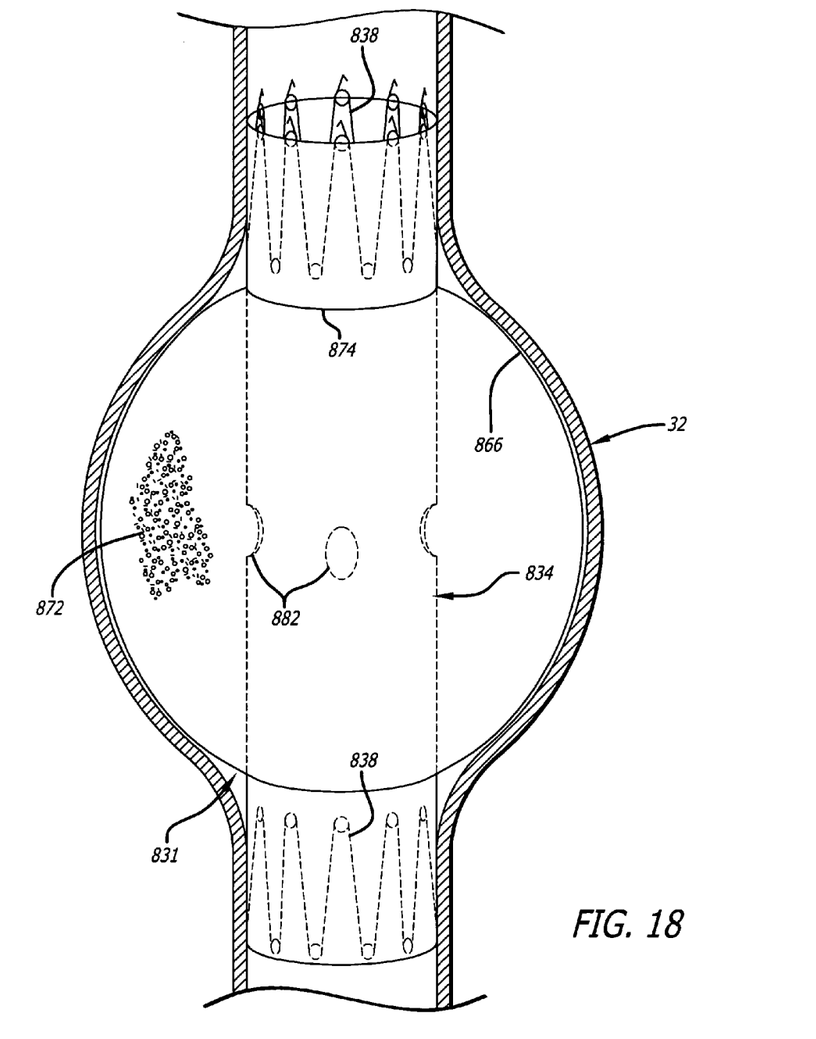
FIG. 18 is a cross-sectional view, depicting the graft of the present invention configured with another variation of a toroid-shaped sealing member.

In another form of the toroid-shaped sealing member 766 (FIG. 17), the sealing member 766 may be fabricated independently of the graft 731, as a complete toroid, which is then connected to an outer wall of the tubular member 734. In yet another form of the toroid-shaped sealing member 866 (FIG. 18), the sealing member 866 may be formed to occupy the majority of the region between the vascular wall 32 and the tubular member 834. In each of the embodiments, attachment systems 738, 838 like those described above can be employed to affixed inferior as well as distal ends of the graft devices 731, 831 to vasculature. Additionally, in each of the embodiments, holes 882 (See FIG. 18) may be configured in the material defining the graft so that the sealing member fills with blood flowing through the graft.

Figure 19:
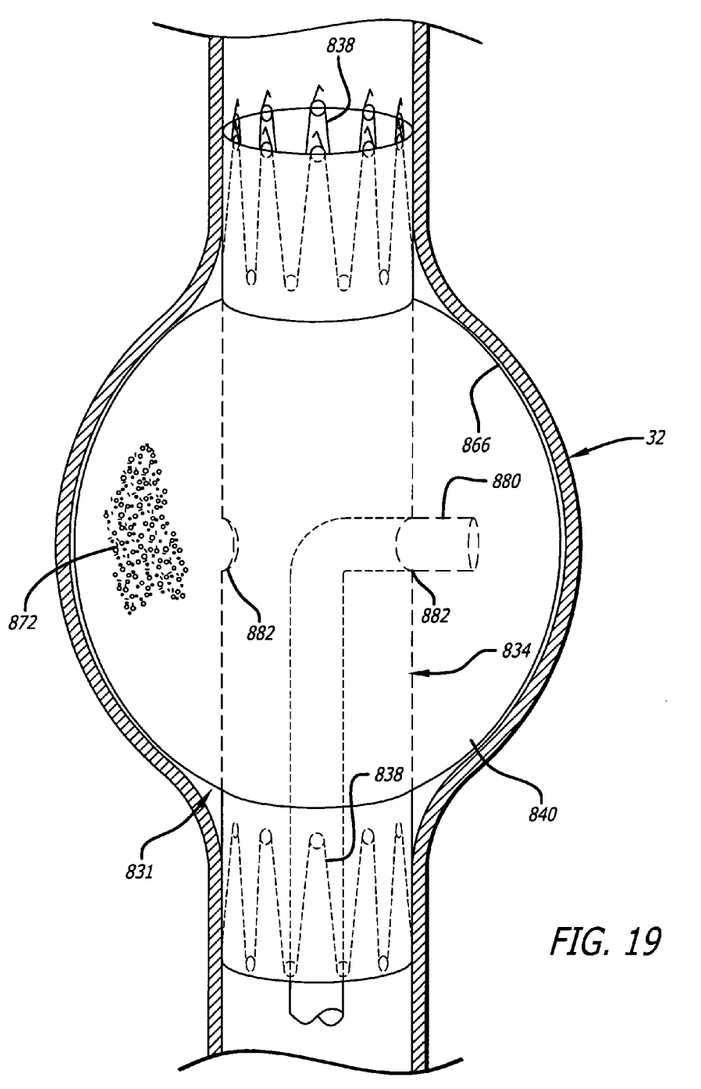
FIG. 19 is a cross-sectional view, showing the graft of FIG. 18 with a tube disposed therein.

Turning now to FIG. 19, there is shown a feed-tube 880 configured to protrude through an aperture 882 formed in the tubular member 834 of the graft 831 to gain access to an internal cavity defined by the sealing member 840. The aperture 882 may be preformed or it can be made by the feed-tube 880 piercing the graft. It is contemplated that such a feed-tube 880 can be used to deliver thrombogenic material to the repair site. The feed-tube 880 may be delivered by a delivery catheter simultaneously with delivery of the improved graft, and may be removed simultaneously with the catheter. Alternatively, the feed-tube 880 can be advanced within the graft 831, after the graft 831 has been deployed within vasculature.

Figure 20:
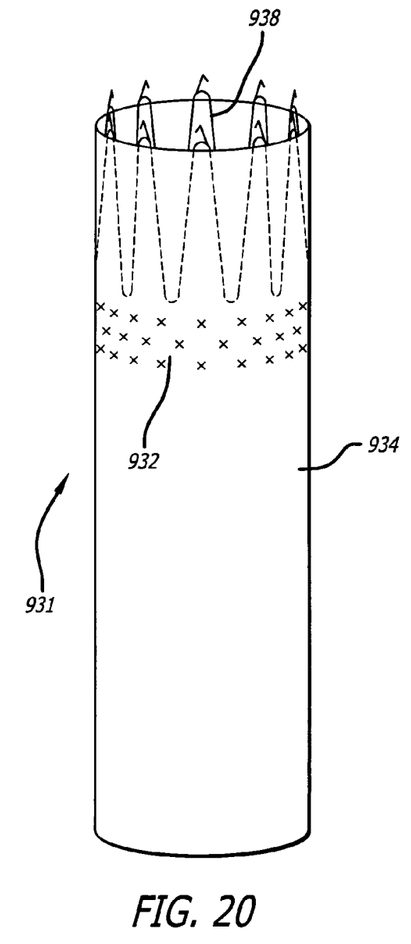
FIG. 20 is a perspective view, depicting a sixth embodiment of the graft of the present invention configured with tufts.
Figure 21:
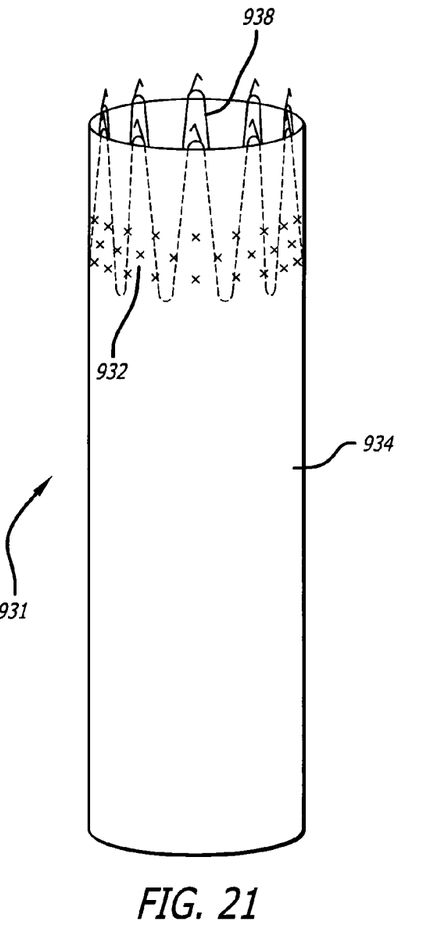
FIG. 21 is a perspective view, depicting a variation of the graft shown in FIG. 20.

In another embodiment (See FIGS. 20 and 21), the graft 931 of the present invention includes a sealing member that is formed from tufted yarn 932, which may be impregnated with thrombogenic substance to induce coagulating, and which is affixed to an outer wall of the tubular member 934 of the graft 931. When the graft is deployed in a diseased vessel (not shown), the tufted yarn 932 operates to fill spaces between the vascular wall and the tubular member 934, thereby substantially forming a seal. In one form of the improved graft 931 having a tufted-yarn sealing member 934, the yarn 932 may be located on the outer surface of the tubular member 934 distal to the attachment system 938 (FIG. 20). In another aspect, the tufted-yam sealing member 931 is located on the outer surface of the graft 931 between members defining the attachment system 938 (See FIG. 21).

Figure 22:
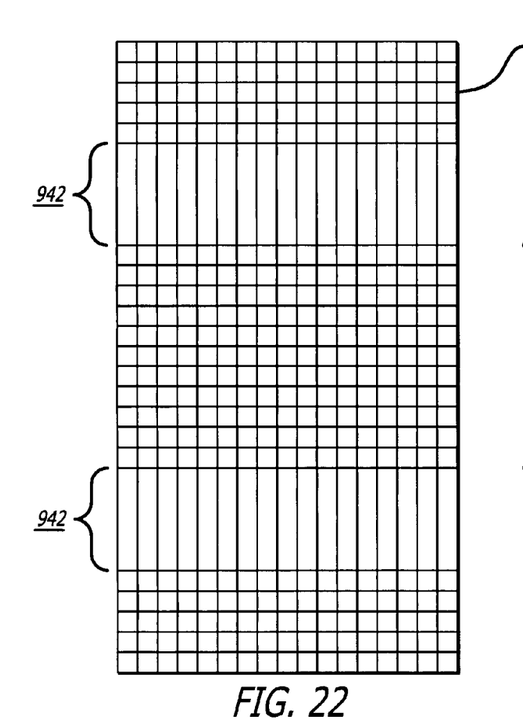
FIG. 22 is a side view, depicting a graft of the present invention.
Figure 23:
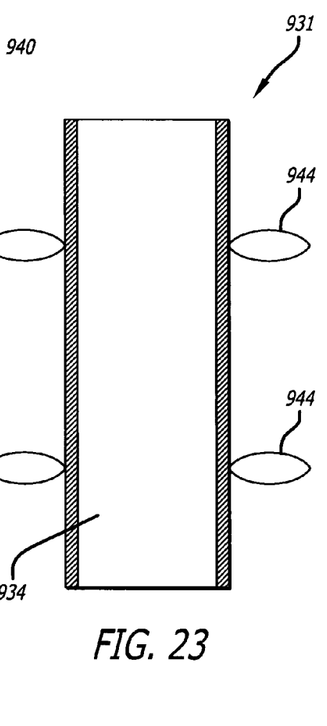
FIG. 23 is a cross-sectional view, depicting a manufacturing step involving the graft shown in FIG. 22.
Figure 24:
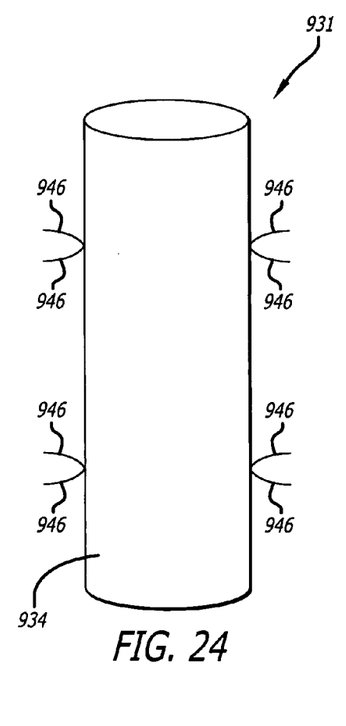
FIG. 24 is a perspective view of the graft shown in FIG. 23 after further processing.

The tufted-yarn sealing member 932, may simply be attached to an outer wall of the graft 931 by stitching the yarn onto the wall of the tubular member 934. The tufts of yarn may be made from the fabric making up the tubular member 934 itself. The fabric 940 (See FIG. 22) from which the graft is manufactured may be woven so that weft threads (running horizontally) are omitted from certain zones 942 thereof. The lengths of warp threads (running vertically) which are not connected to each other by weft threads are pulled radially outward to form a loop 944 (See FIG. 23). The loops of warp thread 944 are cut at the apex of each loop 944, leaving single linear strands of yarn 946 (See FIG. 24) circumferentially protruding from the tubular member 934. The yarn threads may be frayed to provide maximum surface area and if desired, impregnated with a thrombogenic substance.

It will be apparent from the foregoing that, while particular forms of the invention disclosed herein have been illustrated and described, various modifications can be made without departing from the spirit and scope of the invention. Accordingly, it is not intended that the invention be limited, except as by the appended claims.

We claim:

1. A graft, comprising:
   a tubular member;
   a sealing member configured to substantially prevent fluid leakage therethrough connected to said tubular member and being configured to surround said tubular member, the sealing member including a free end unconnected to the tubular member; and
   a biasing member connected to said sealing member and configured to provide said sealing member with a frustoconical profile, the free end of the sealing member being biased away from the tubular member by the biasing member.

2. The graft of claim 1, said biasing member further comprising a generally undulating frame.

3. The graft of claim 1, wherein said sealing member is disc-shaped.

4. The graft of claim 3, said biasing member further comprising a generally undulating wire frame.

5. The graft of claim 3, said biasing member further comprising a wire hoop.

6. The graft of claim 3, wherein said biasing member is configured to provide said sealing member with a generally uniform force along said frustoconical profile.

7. The graft of claim 1, wherein said biasing member is attached to an inside surface of said sealing member.

8. The graft of claim 1, wherein said biasing member is attached to an outside surface of said sealing member.

* * * * *